(12) United States Patent
Tonelli et al.

(10) Patent No.: US 7,935,072 B2
(45) Date of Patent: May 3, 2011

(54) METHOD OF MONITORING THE OPERATIONALITY OF A FLOW CUT-OFF MEMBER AND FLOW ARRESTING SYSTEM, FOR AN EXTRACORPOREAL FLUID CIRCUIT

(75) Inventors: Claudio Tonelli, Modena (IT); Marco Paraluppi, Medolla (IT)

(73) Assignee: Gambro Lundia AB (SE)

( * ) Notice: Subject to any disclaimer, the term of this patent is extended or adjusted under 35 U.S.C. 154(b) by 395 days.

(21) Appl. No.: 12/124,516

(22) Filed: May 21, 2008

(65) Prior Publication Data

US 2008/0234620 A1 Sep. 25, 2008

Related U.S. Application Data

(62) Division of application No. 10/505,150, filed on Aug. 20, 2004, now Pat. No. 7,393,337.

(30) Foreign Application Priority Data

Feb. 22, 2002 (IT) .............................. MI2002A0359

(51) Int. Cl.
*A61M 37/00* (2006.01)
*G01L 1/04* (2006.01)
(52) U.S. Cl. .................................. 604/6.1; 73/862.621
(58) Field of Classification Search .................. 604/4.01, 604/5.01, 6.1, 250; 73/862.621; 251/4
See application file for complete search history.

(56) References Cited

U.S. PATENT DOCUMENTS

| | | | |
|---|---|---|---|
| 3,830,234 A | 8/1974 | Kopp | |
| 4,298,938 A | 11/1981 | Wang et al. | |
| 4,421,503 A | 12/1983 | Latham, Jr. et al. | |
| 4,614,590 A | 9/1986 | Rath et al. | |
| 4,634,426 A | 1/1987 | Kamen | |
| 4,925,152 A | 5/1990 | Hüber | |
| 5,141,492 A | 8/1992 | Dadson et al. | |
| 5,371,329 A | 12/1994 | Fillaud | |
| 5,423,323 A | 6/1995 | Orth | |
| 5,633,168 A | 5/1997 | Glasscock et al. | |
| 5,679,245 A | 10/1997 | Manica | |
| 5,776,091 A | 7/1998 | Brugger et al. | |
| 5,863,421 A | 1/1999 | Peter, Jr. et al. | |
| 5,989,438 A | 11/1999 | Fumiyama | |
| 6,012,342 A | 1/2000 | Blight et al. | |
| 6,221,040 B1 | 4/2001 | Kleinekofort | |
| 6,386,505 B2 | 5/2002 | Schob | |

FOREIGN PATENT DOCUMENTS

| | | |
|---|---|---|
| DE | 3720667 | 5/1989 |
| DE | 4013402 | 7/1991 |
| DE | 4003452 | 8/1991 |

(Continued)

*Primary Examiner* — Leslie R Deak
(74) *Attorney, Agent, or Firm* — Finnegan, Henderson, Farabow, Garrett & Dunner, LLP

(57) ABSTRACT

A description is given of a method of monitoring the operationality of a flow cut-off member for an extracorporeal fluid circuit. Also described is a system for arresting the flow of blood that implements this monitoring method. The system has a flow cut-off member active on a radially deformable length of tube forming part of the circuit, and a unit capable of causing a movement of a movable portion of the cut-off member towards a closed condition. The system detects when the movable portion passes through a first predetermined position and determines the value assumed by a dynamic parameter associated with the motion of the movable portion at the first predetermined position. The system further checks that this value is within a predetermined criterion of acceptability. Lastly, a blood treatment appliance is described that implements the described method and system.

24 Claims, 1 Drawing Sheet

FOREIGN PATENT DOCUMENTS

| | | |
|---|---|---|
| DE | 19900320 | 6/2000 |
| EP | 0 551 418 B1 | 7/1983 |
| EP | 0 088 900 B1 | 9/1983 |
| EP | 0 238 809 B1 | 9/1987 |
| EP | 0 229 354 B1 | 7/1991 |
| EP | 0 565 585 B1 | 10/1993 |
| EP | 0 578 175 B1 | 1/1994 |
| EP | 0 643 301 B1 | 3/1995 |
| EP | 0 718 008 B1 | 6/1996 |
| EP | 1 086 712 A2 | 3/2001 |
| EP | 1 086 712 A3 | 3/2001 |
| EP | 1 132 108 A1 | 9/2001 |
| EP | 0 718 001 B1 | 6/2002 |
| FR | 2 379 290 | 9/1978 |
| GB | 2 225 954 | 6/1990 |
| WO | WO 90/07353 | 7/1990 |
| WO | WO 91/12834 | 9/1991 |
| WO | WO96/25214 | 8/1996 |
| WO | WO 00/12991 | 3/2000 |

METHOD OF MONITORING THE OPERATIONALITY OF A FLOW CUT-OFF MEMBER AND FLOW ARRESTING SYSTEM, FOR AN EXTRACORPOREAL FLUID CIRCUIT

This is a division of application Ser. No. 10/505,150, filed Aug. 20, 2004 now U.S. Pat. No. 7,393,337, which claims the benefit of priority of Italian Application No. MI2002A000359, filed on Feb. 22, 2002, both of which are incorporated herein by reference.

The present invention relates to a method of monitoring the operationality of a flow cut-off member for an extracorporeal fluid circuit; the invention also relates to a flow arresting system for an extracorporeal fluid circuit.

In particular, the invention is of application in ensuring the correct functioning of a flow cut-off member operating on a blood return line to the patient in an extracorporeal circuit connected to a blood treatment appliance. The invention can also be applied to carrying out an operation on the abovementioned flow cut-off member if it is found to be malfunctioning.

As is known, appliances for treating blood in an extracorporeal circuit, such as appliances for treating renal insufficiency by haemodialysis, haemofiltration, or haemodiafiltration, plasmapheresis appliances, etc, use an extracorporeal circuit to carry the blood taken from a patient to a blood treatment unit. This unit normally consists of a containment body defining at least one first chamber, for incoming blood, and at least one second chamber, designed to receive the unwanted particles and/or excess fluid present in the blood (or the plasma in the case of plasmapheresis). The two chambers are separated from each other by a semipermeable membrane.

The first chamber of the treatment unit is then connected, downstream with respect to the direction of movement of the blood, to a return branch or line carrying the blood back to the patient.

The terminal portion of the blood return line is normally fitted with an access member, such as a needle or other device, for connecting the extracorporeal circuit to the patient's vascular system.

Immediately upstream of this access member there is typically a flow interruption member, generally a clamp or pinch valve, capable of closing upon a length of tube of the blood return line to the patient.

In greater detail, the pinch value has at least one movable portion designed to move between an open condition, in which flow is allowed along the tubing, and a closed condition, in which the movable part of the valve moves towards its fixed part, compressing the tube and therefore cutting off the flow of fluid through the tube.

In the uses described above, the pinch valve acts as the final safety device, capable of cutting off the flow of blood to the patient immediately any malfunction or any danger to the patient arises.

For this purpose, the pinch valve may be controlled by a monitoring unit communicating with sensors or transducers that pass to this monitoring unit signals about potentially dangerous situations. For example, the monitoring unit may be linked to an air bubble detection unit active on the extracorporeal circuit upstream of the pinch valve: in the event of air bubbles large enough to create a situation of potential danger to the patient, the monitoring unit closes the clamp, preventing the bubble from getting into the vascular system of the patient.

In order to be able to ensure operationality of the pinch valve, the latter is typically equipped with a position sensor for detecting when the movable part has reached a predetermined position (taken to correspond to closure of the tube) relative to the fixed part, upon which it sends a corresponding signal to the monitoring unit. In practice, the position sensor checks that, in flow cut-off conditions, the movable part of the clamp is separated from the lower fixed part by a predefined distance, approximately corresponding to the total thickness of the walls of the tube when compressed by the valve.

It is obvious that, given their nature, the position sensors connected to the cut-off systems described above are only able to supply an on-off type indication, i.e. they are only able to decide whether the movable part has reached a predetermined position of closure relative to the fixed part and possibly to recognize the presence or absence of a tube in the correct position inside the clamp.

Although widely used, the flow cut-off devices described briefly above have a number of limitations.

In the first place, devices with a pinch valve and position sensor cannot give information about how the valve carries out the transition to closure or relate the transition to closure of the valve to the manner in which the dangerous event is propagating towards the zone of access to the patient.

Still referring to a situation in which a detector device has reported the presence of an air bubble of excessive size in a predetermined zone of the extracorporeal circuit, the ideal solution would be to succeed in completely cutting off the flow of blood to the patient before the volume of blood present between the section containing the bubble and the patient access point is completely exhausted. Clearly, if the clamp does not work fast enough, there is a risk of the dangerous event (in this case the air bubble) being transferred into the cardiovascular system of the patient. It should be stressed however that in reality there are numerous factors that can influence the operation of the safety clamp; to cite just a few: the theoretical speed of response of the chain from danger detecting sensor to CPU to valve, the speed of propagation of the dangerous event along the extracorporeal circuit, the actual efficiency of the valve, the mechanical properties of the length of tube subject to compression, etc.

It should also be noted that, in known systems, all that can be found out is whether or not the movable part or parts of the valve have reached a predetermined relative position unrelated to the actual geometry of the length of tube subject to compression; owing to manufacturing tolerances, the actual dimensions of the tube may obviously differ from one line to another, despite being of the same nominal dimensions. In practice, the thickness of the walls of the length of tube on which the valve acts varies between minimum and maximum values in a predetermined tolerance range. Therefore, although the closing action may be the same, the compression of the tube may be correct, excessive or too little, depending on the actual dimensions of the tube in question. It should be remembered here that the position sensor is designed to detect when the movable part of the clamp reaches a predetermined position; this position corresponds to a distance between the cooperating parts of the valves at which, theoretically, the flow through the tube would be cut off, assuming that the maximum wall thickness of the tube is in a tolerance range judged to be acceptable. This design decision avoids undesirable situations of false alarms but does not ensure that actual flow cut-off is monitored, particularly when the tube has walls of the minimum thickness even if within a tolerance judged to be acceptable. The effects described above can be aggravated if the pinch valve is operated repeatedly on the same length of tube (as occurs for example in single-needle treatments), causing deterioration to the material and/or permanent deformations thereof.

SUMMARY OF THE INVENTION

In light of the above, it is a fundamental object of the present invention to solve all of the problems described above that are typical of the prior art.

In particular, it is an object of the invention to provide a method capable of ensuring that a flow cut-off member, for example a clamp, is operating correctly as it moves through its transition to closure.

In addition, it is an object of the invention to provide a novel method capable of interacting with the flow cut-off member, so that the latter works reliably even in problematical working situations, such as malfunctions of the flow cut-off member, slow response of the various parts designed to activate the flow cut-off member, geometrical errors or tube positioning errors, etc.

Lastly, it is an object of the invention to provide a flow arresting system, especially for extracorporeal blood-treatment appliances, that is capable of implementing the above-mentioned monitoring method.

These and other objects, which will become clearer in the course of the following description, are basically achieved with a method and system in accordance with the appended claims.

Other features and advantages will become apparent in the course of a detailed description of a preferred, but not exclusive embodiment of a method and system in accordance with the invention.

BRIEF DESCRIPTION OF THE DRAWINGS

This description will be given below with reference to the appended figures, which are provided purely for guidance and are therefore not limiting, in which.

DETAILED DESCRIPTION

Figure 1:
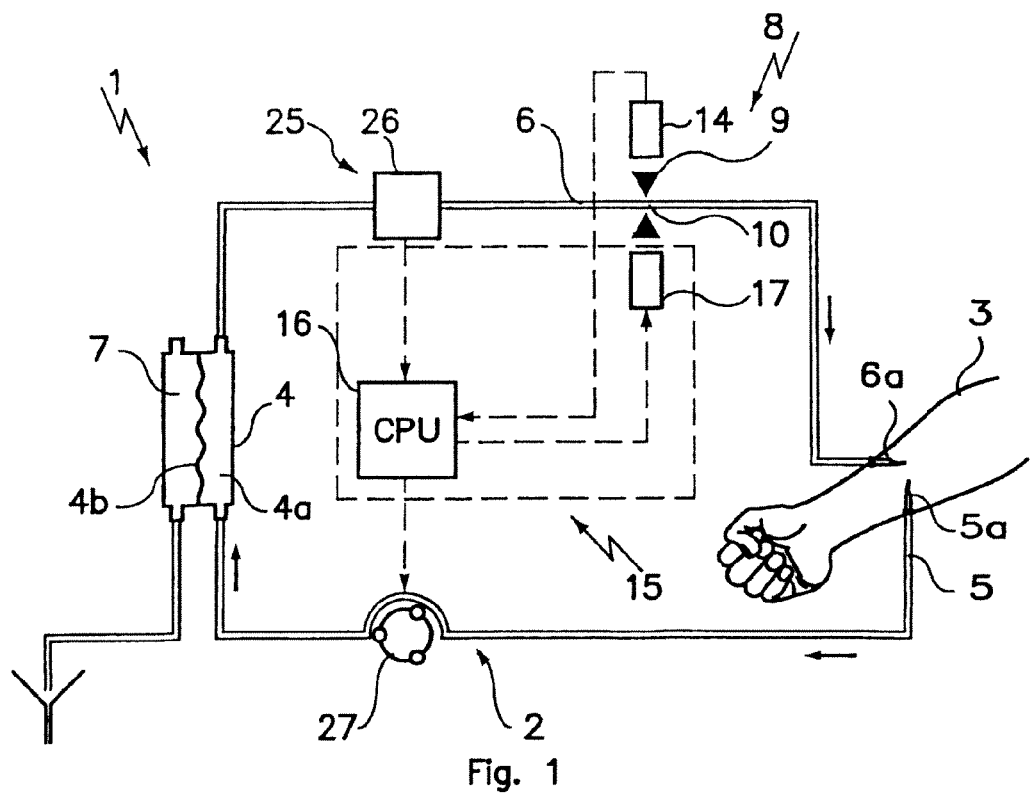
FIG. 1 relates to a general diagram of an extracorporeal blood-treatment appliance that implements the method and system in accordance with the invention.

Referring to FIG. 1, an extracorporeal blood-treatment appliance is indicated as a whole by the number 1. The appliance 1 may be, for example, a haemodialysis and/or haemofiltration and/or haemodiafiltration and/or ultrafiltration and/or plasmapheresis appliance. The appliance 1 comprises an extracorporeal circuit 2 designed to carry blood from a patient 3 to a blood-treatment unit 4 and then return the blood, suitably treated, to a return zone where the blood is returned to the patient. For this purpose the extracorporeal circuit typically has a first access member 5a in fluid communication with a blood collecting line 5 leading to an entry zone where the blood enters the treatment unit 4. The extracorporeal circuit also includes a blood return line 6 leading to a second access member 6a connecting to the patient's cardiovascular system for return of the blood to the patient. As an equivalent to the structure described, a single access member may be connected alternately to the blood collecting line and then to the blood return line.

The blood treatment unit comprises a containment body defining at least two chambers 4a, 4b separated from each other by a semipermeable membrane 7. The first chamber 4a receives blood to be treated from the extracorporeal circuit briefly described above. In the case of haemodialysis, haemofiltration, ultrafiltration or haemodiafiltration treatments, the second chamber is designed to receive unwanted particles and/or excess liquid for removal from the patient's blood. In the case of plasmapheresis, the treatment unit 4 also includes a plasma filter.

The appliance 1 comprises a system 8 for arresting the flow of fluid, in this case blood, which will be described in detail below.

Figure 2:
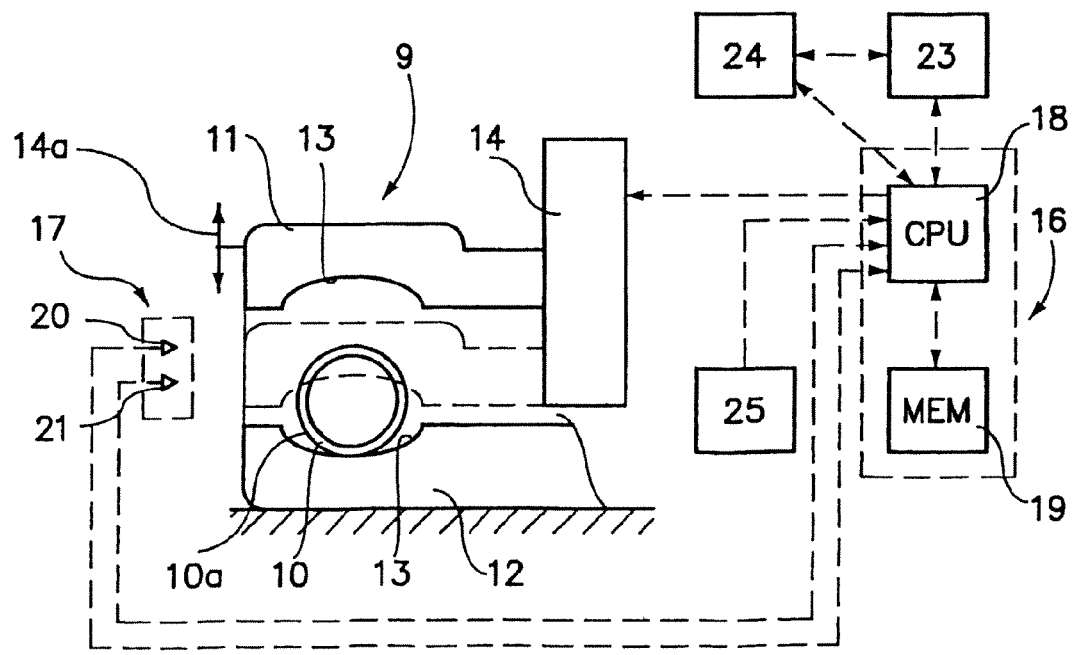
FIG. 2 illustrates schematically and in cross section a portion of tube on which a flow cut-off member acts, forming part of a flow arresting system according to the invention.

The system 8 acts on at least one flow cut-off member 9 operating on a length of deformable tubing 10 of the extracorporeal circuit; in particular, the flow cut-off member operates between an open condition, in which it allows the fluid to pass through, and at least one closed condition, in which it prevents the fluid passing along the said length of tube. In the example illustrated in FIG. 1 the cut-off member is positioned on the return line 6 taking the blood back to the patient, close to and upstream of the second access member 6a. In more detail, it should be observed that the cut-off member comprises at least one movable portion 11 designed to move towards and away from a fixed portion 12. As illustrated in the example in FIG. 2, the movable portion and the fixed portion together define a housing seat 13 in which the abovementioned length of tubing 10 sits. Because of the radial deformability of the length of tubing 10, the movement of the movable portion towards the fixed portion of the cut-off member causes progressive compression of the length of tubing, which therefore changes from an open condition, illustrated in FIG. 2, to a closed condition in which the side walls of the tube come together and cut off the flow of fluid. Movement of the movable member as described above is provided by an actuator 14 connected to the cut-off member 14. The actuator 14 may be of any type capable of bringing about a closing movement of the movable portion towards the fixed portion; in particular, a hydraulic, pneumatic, electric, electromagnetic, mechanical or any other type of actuator may be used. The actuator 14 acts under the control of a monitoring unit 15 connected to the said actuator.

The monitoring unit 15 of the system illustrated comprises a control unit 16, and means 17 for detecting a sequence of placings of the said movable portion in successive positions, sending corresponding signals to the said monitoring unit. In terms of construction, the monitoring unit comprises at least one microprocessor block 18, or CPU, and a memory 19 for the CPU. The detector means 17 meanwhile comprise one or more position sensors. In the example illustrated, there are two position sensors 20, 21 capable of detecting when the movable part 11 reaches two corresponding positions spaced apart from each other. The position sensors may for example be optical sights designed to send corresponding consent signals to the CPU 18 for the movement of the said movable portion 11.

The monitoring unit is also connected to a user interface 22 comprising an output device 23, such as a video display or the like, and an input device 24 comprising data reading means and/or a keyboard.

From the operating point of view, the system 8 behaves as described below. When a situation of danger is detected, the monitoring unit 15 sends a signal to the actuator to close the cut-off member as a safety function to prevent the event that has been judged to be dangerous from reaching the patient's cardiovascular system. In practice, by integrating the system 8 with sensor means 25 designed to detect predetermined monitoring parameters ($p_c$) of correct operation of the said appliance, the system 8 acts whenever a situation judged to be dangerous is detected. Note that the monitoring parameters may be, for example, the size of air bubbles that may be present in the blood, the temperature of the blood and/or the temperature of the dialysis liquid, the pH of the dialysis liquid, the pressure of the blood and/or of the dialysis liquid, etc. In the example illustrated, the sensor means comprise an air bubble detector 26 connected to the extracorporeal circuit, on line 6.

Besides acting as a closure system, the system 8 checks that the cut-off member is working properly when it closes: in this case the monitoring unit 15 implements a method of monitoring the cut-off member for correct operation. The system 8, or more precisely the monitoring unit 15, runs a check on the operationality of the cut-off member whenever:

- a periodic preprogrammed automatic command (occurring every n minutes) autonomously activates the system 8, thus checking the cut-off member for correct operationality during closure;
- a preprogrammed automatic command autonomously activates the system 8 at the beginning of each treatment, thus checking the cut-off member for correct operationality during closure;
- a dangerous event has caused the cut-off member to close; in practice, if the cut-off member is activated, its operationality is checked simultaneously; if the cut-off member does not operate as desired the monitoring unit can intervene directly to modify the action of the cut-off member. In this last case, in practice, the monitoring unit both checks and controls the cut-off member.

Turning now to the detail of the functional description, whenever a manual command, an automatic command or a particular event triggers its actuation, the monitoring unit 15 is capable of sending a signal to the said actuator 14 to move the movable portion (in the directions identified by the arrow 14a) of the cut-off member between a rest position, which corresponds to the open condition of the cut-off member and hence the passage of fluid through the said length of tubing, and a working condition, in which the movable portion acts to compress the portion of tube 10 to cut off the flow.

Notice that in the rest position the movable portion is typically at a distance from the surface 10a of the tube 10 and comes into contact with the latter during the movement towards the closed condition.

The monitoring unit 15 is also responsible for associating with the movable portion 11 at least one dynamic parameter p capable of providing an at least partial indication of the condition of motion of the movable portion during its movement from the rest position to the working position. It should be noted that a single dynamic parameter may be used, or a plurality of different dynamic parameters.

The monitoring unit 15 therefore determines a value V assumed by the said dynamic parameter or parameters when the movable part passes through a first position which the movable part can adopt during movement from the rest condition to the working condition. As an example, if the dynamic parameter in question is the speed of the movable part during the transition from the rest condition to the working condition, the monitoring unit will assess an average speed value assumed by the movable part in a neighbourhood of the said first position; alternatively, if the dynamic parameter is a time interval, the monitoring unit will determine the time taken by the movable part 11 to move for example from the rest position to the said first position or, alternatively, the time interval taken by the movable part 11 to move from the first position to a second position at a distance from and subsequent to the first position.

Once the monitoring unit has determined the actual value assumed by the predetermined dynamic parameter when the movable part is in a certain first position during its movement, the monitoring unit checks that this value satisfies a predetermined criterion of acceptability. In other words, still referring by way of example to the case in which the parameter is speed, the monitoring unit compares the average speed of the movable portion at a predetermined first position with a criterion of acceptability. This criterion of acceptability may be of predetermined type, such as a minimum speed capable of closing the cut-off member quickly enough. Alternatively, the criterion of acceptability may be calculated by the monitoring unit as a function of other factors, for example as a function of:

- pi, corresponding to or proportional to the pressure in the vicinity of the length of tube when the cut-off member is in the open condition;
- fl, corresponding to the rate of flow of fluid through the length of tube when the cut-off member is in the open condition.

Returning to the description of the operating phases initiated by the system 8, it should be observed that the first position in which the value assumed by the abovementioned dynamic parameter is determined is a position preferably intermediate between the rest position of the movable part and the working position of the same movable part. In greater detail, the first position is intermediate between the ideal working position (complete closure of the tubing 10 with tube of exactly nominal dimensions) and a position of initial contact between the movable portion and the outer surface of the length of tubing.

As has been mentioned earlier the dynamic parameter is designed to describe a condition of motion of the movable portion.

In this regard, this parameter is selected from the group comprising the following dynamic parameters:

a) p1, corresponding to a time interval dT taken by the movable part to move between the first predetermined position and a second predetermined position at a distance from the said first position, b) p2, corresponding to a speed of the said movable part at the said first position, c) p3, corresponding to an acceleration of the said movable part at the said first position, d) p4, corresponding to a function F(p1) of the said parameter p1, e) p5, corresponding to a function F(p2) of the said parameter p2, f) p6, corresponding to a function F(p3) of the said parameter p3, and g) p7, corresponding to a function of one or more of the parameters p1, p2, p3.

To summarize, if the dynamic parameter p is linked to a time interval or to a function of a time interval, the monitoring unit calculates the value of the said parameter p as the time dT (or as a function of the time dT) taken by the movable part to move from the first position to a second position at a distance from the first position. Once the time interval used by the movable portion to carry out a predetermined movement between two positions has been calculated, this time interval is compared with the criterion of acceptability. Alternatively the time interval may be determined and, therefore, a function proportional to this time interval is calculated in order to then compare it with a criterion of acceptability. If the dynamic parameter associated with the movable portion is the speed or a magnitude that is a function of the speed (kinetic energy, momentum or the like), the monitoring unit arranges for calculation of an average speed assumed by the movable portion in a neighbourhood of the said first position in order to then compare it with the said criterion of acceptability. Lastly, if the dynamic parameter is an acceleration or a function of the acceleration of the movable portion (resulting from the forces acting on the movable portion), the monitoring unit arranges for calculation of an average acceleration of the movable portion in a neighbourhood of the said position. Where the dynamic parameters consist of vectorial physical quantities, the important part is obviously calculating at least one component of these vectorial quantities in the direction followed by the movable part as it approaches the fixed part of the cut-off member.

Note that the parameter p or the parameters pi can be determined by analogue sensors that output a continuous signal proportional to the instantaneous value of the parameter. In all cases, the monitoring unit arranges for a comparison between the analogue profile of the parameter p with a criterion of acceptability.

Note that the monitoring unit associates one, two or more parameters with the movable portion, each parameter being designed to give different dynamic information about the motion of the movable portion as it advances towards the fixed portion.

In one possible alternative, the monitoring unit is designed to carry out, for each dynamic parameter, a plurality of phases of determining values Vi assumed by that dynamic parameter at successive predetermined positions assumed by the movable part during its movement. Each value of the parameter in successive positions is however determined essentially as described above.

By carefully selecting the dynamic parameters and the criterion of acceptability, it is possible to work out precisely how the movable portion of the cut-off member is moving from the rest position towards the working position. In other words it is possible to know the speed of closure of the movable portion of the cut-off member and be sure that the action of the cut-off member is as it should be (the system is therefore exercising a function of control of the closure action) or at any rate be sure that a situation of incorrect operationality is reported.

It should indeed be noted that if the value assumed by the dynamic parameter or by a predetermined number of dynamic parameters (if more than one is being used) is not within a range of acceptability (or does not satisfy a criterion of acceptability), the monitoring unit can initiate an alarm signaling procedure and/or a corrective procedure (control). Notice here that the appliance 1 is provided with a user interface 22 equipped with a display by means of which the monitoring unit can send an optical or acoustic signal about the alarm condition. The monitoring unit can also, depending on the situation, coordinate stoppage of the treatment which the appliance 1 is performing should the abovementioned alarm condition occur.

As mentioned, the monitoring unit is also capable of activating a correction phase whereby the monitoring unit intervenes on the actuator 14 to modify its action on the movable portion of the cut-off member, in the light of the difference between the value of the dynamic parameter and a limit value judged to be acceptable for that parameter. In practice, if a reading of time, speed or acceleration throws up an incorrect response by the cut-off member, e.g. the movable part 11 is moving too slowly or excessive load is being transmitted to the length of tubing 10, the monitoring unit activates the actuator member in such a way as to increase or reduce the closing speed and/or force of the movable part. It will be clear that if the system is used for control, that is to say acting on the actuator to regulate the closing action of the cut-off member, then not only will there be a significant advantage of increased operational reliability, but also the possibility of damage to the tube and formation of cracks or detachments of parts of the tube is greatly reduced.

Alternatively, or in coordination with what is described above, the monitoring unit may act on means 27, such as a peristaltic pump, designed to set up a flow of liquid within the extracorporeal circuit, in such a way as to vary the rate of the said flow. In practice, if the movement of the movable portion has been found to be too slow, the actuator can be used to increase its speed, and the pump 27 connected to the extracorporeal circuit can be used simultaneously or alternatively to slow down the rate of flow of fluid through the circuit tubing. By this means, any dangerous event that is using the extracorporeal circuit as a means of propagation is clearly slowed down, allowing the cut-off member to close the circuit safely and cut off the flow towards the patient.

The invention claimed is:

1. A system for arresting the flow through an extracorporeal fluid circuit comprising:
   at least one active flow cut-off member coupled to a length of deformable tubing forming part of said extracorporeal fluid circuit, said cut-off member having at least one movable portion and being actuatable between an open condition, said open condition allowing the fluid to pass through, and at least one closed condition, said at least one closed condition preventing the fluid from passing through said length of deformable tube;
   an actuator connected to said cut-off member for moving at least said movable portion; and
   a monitoring unit coupled to said actuator and capable of:
      causing a movement of the movable portion of the cut-off member towards said closed condition;
      determining a value of at least one dynamic parameter associated with a motion of said movable portion during said movement; and
      checking that the value assumed by said dynamic parameter satisfies a criterion of acceptability;
   wherein said at least one dynamic parameter is determined in relation to a first position of the movable portion, said first position being intermediate between a rest position and a working position, said movable portion being in the working position when the cut-off member is in the closed condition, and said movable portion being in the rest position when the cut-off member is in the open condition; and
   wherein said at least one dynamic parameter is configured to provide information about a condition of motion of said movable portion and is selected from:
      p1, corresponding to a time interval dT taken by the movable portion to move between a first predetermined position and a second predetermined position, at a distance from said first predetermined position,
      p2, corresponding to a speed of said movable portion at said first predetermined position,
      p3, corresponding to an acceleration of said movable portion at said first predetermined position,
      p4, corresponding to a function F(p1) of said parameter p1,
      p5, corresponding to a function F(p2) of said parameter p2,
      p6, corresponding to a function F(p3) of said parameter p3, and
      p7, corresponding to a function of two or more of said parameters p1, p2, p3.

2. A system according to claim 1, wherein the cut-off member comprises a fixed portion defining, in conjunction with said movable portion, a housing seat for said length of deformable tubing, the movable portion being configured, when moving towards the closed condition, to approach the fixed portion to progressively compress said length of deformable tubing.

3. A system according to claim 1, wherein said monitoring unit is designed to calculate the value of said at least one dynamic parameter, said value being the time interval dT taken by said movable portion to move from the first predetermined position to the second predetermined position, the second predetermined position being subsequent to and at a distance from the first predetermined position.

4. A system according to claim 3, wherein said monitoring unit is designed to determine the value of said at least one dynamic parameter, said value being the time interval dT taken by the movable portion to move from the rest position, said rest position corresponding to the open condition of the cut-off member, to the first predetermined position.

5. A system according to claim 1, wherein said monitoring unit is designed to carry out a plurality of steps to determine values Vi assumed by said dynamic parameter at successive predetermined positions of the movable portion during said movement.

6. A system according to claim 5, wherein said monitoring unit is configured to activate a correction step, generate an alarm, or activate a correction step and generate an alarm, if a predetermined number of said values Vi are not within respective ranges of acceptability.

7. A system according to claim 1, wherein the monitoring unit is configured to activate a subsequent correction and/or alarm step if said value of the at least one dynamic parameter does not satisfy the criterion of acceptability.

8. A system according to claim 7, wherein the monitoring unit is configured to control said actuator to vary at least a speed of movement of the movable portion of said cut-off member.

9. A system according to claim 7, wherein the monitoring unit is configured to execute said steps in response to a detection of a dangerous situation.

10. A system according to claim 1, wherein said criterion of acceptability is predetermined.

11. A system according to claim 1, wherein said monitoring unit is capable of calculating the criterion of acceptability as a function of:
  pi, corresponding to or proportional to the pressure in a vicinity of the length of deformable tube when the cut-off member is in the open condition; or
  f1, corresponding to the rate of flow of fluid through the length of tube when the cut-off member is in the open condition.

12. A system according to claim 1, wherein said monitoring unit comprises:
  a control unit, and
  a device configured to detect at least one location of said movable portion among a plurality of successive positions, said device sending at least one corresponding signal to the control unit, said control unit determining a value of said at least one dynamic parameter in response to said at least one signal.

13. A system according to claim 12, wherein said device comprises position sensors connected to said control unit.

14. A system according to claim 12, wherein the control unit comprises at least one microprocessor block, and a memory connected to the at least one microprocessor block.

15. A system according to claim 12, wherein the control unit comprises at least one central processing unit (CPU), and a memory connected to the at least one central processing unit or CPU.

16. A system according to claim 1, wherein the monitoring unit is configured to execute said steps in response to an automatic preprogrammed command.

17. A blood treatment appliance comprising:
  an extracorporeal circuit equipped with at least one blood treatment unit, said at least one blood treatment unit having at least first and second chambers, said at least first and second chambers being separated from each other by a semi-permeable membrane;
  at least one collecting line configured to collect blood from a patient; said at least one collecting line being connected to an inlet of said first chamber;
  at least one second line for returning the blood to the patient, said at least one second line being in fluid communication with an outlet of the said chamber; and
  an apparatus for setting up a flow of fluid through said extracorporeal circuit, wherein said apparatus comprises a system according to claim 1.

18. An appliance according to claim 17, comprising at least one sensor for detecting predetermined parameters to monitor a correct operation of said appliance, said at least one sensor being configured to send corresponding signals to the monitoring unit for determination of potential undesired conditions.

19. An appliance according to claim 17, wherein said at least one sensor comprises an air bubble detector connected to the extracorporeal circuit.

20. An appliance according to claim 18, wherein, upon determination of said undesired conditions, the monitoring unit sends commands for closure of the cut-off member and for carrying out the steps of:
  moving the movable portion of the cut-off member from said open condition towards said closed condition;
  associating at least one dynamic parameter with a motion of said movable portion;
  determining a value of said at least one dynamic parameter relating to said movable portion at least during said movement; and
  checking that the value assumed by said at least one dynamic parameter satisfies a predetermined criterion of acceptability.

21. A unit for monitoring the operationality of a member for cutting off the flow of a fluid in an extracorporeal circuit, said unit being programmed to carrying out the following steps:
  moving a movable portion of the cut-off member from an open condition towards a closed condition;
  associating at least one dynamic parameter with a motion of said movable portion;
  determining a value of said at least one dynamic parameter relating to said movable portion at least during said movement; and
  checking that the value assumed by said at least one dynamic parameter satisfies a predetermined criterion of acceptability;
  wherein said at least one dynamic parameter is determined in relation to a first position of the movable portion, said first position being intermediate between a rest position and a working position, said movable portion being in the working position when the cut-off member is in the closed condition, and said movable portion being in the rest position when the cut-off member is in the open condition; and
  wherein said at least one dynamic parameter is configured to provide information about a condition of motion of said movable portion and is selected from:
  p1, corresponding to a time interval dT taken by the movable portion to move between a first predetermined position and a second predetermined position, at a distance from said first predetermined position, p2, corresponding to a speed of said movable portion at said first predetermined position, p3, corresponding to an acceleration of said movable portion at said first predetermined position, p4, corresponding to a function F(p1) of said parameter p1, p5, corresponding to a function F(p2) of said parameter p2, p6, corresponding to a function F(p3) of said parameter p3, and p7, corresponding to a function of two or more of said parameters p1, p2, p3.

22. A system for arresting the flow through an extracorporeal fluid circuit comprising:

at least one active flow cut-off member coupled to a length of deformable tubing forming part of said extracorporeal fluid circuit, said cut-off member having at least one movable portion and being actuatable between an open condition, said open condition allowing the fluid to pass through, and at least one closed condition, said at least one closed condition preventing the fluid from passing through said length of deformable tube;

an actuator connected to said cut-off member for moving at least said movable portion; and a monitoring unit coupled to said actuator and programmed to perform steps of:

causing a movement of the movable portion of the cut-off member towards said closed condition;

determining a value of at least one dynamic parameter associated with a condition of motion of said movable portion during said movement at a position between a rest position and a working position; and checking whether the value of said dynamic parameter satisfies a criterion of acceptability.

23. A system according to claim 22, wherein said dynamic parameter is determined in relation to a first position of the movable portion, said first position being intermediate between said rest position and said working position, said movable portion being in the working position when the cut-off member is in the closed condition, and said movable portion being in the rest position when the cut-off member is in the open condition.

24. A device according to claim 22, wherein said at least one dynamic parameter is selected from:

p1, corresponding to a time interval dT taken by the movable portion to move between a first predetermined position and a second predetermined position, at a distance from said first predetermined position, p2, corresponding to a speed of said movable portion at said first predetermined position, p3, corresponding to an acceleration of said movable portion at said first predetermined position, p4, corresponding to a function F(p1) of said parameter p1, p5, corresponding to a function F(p2) of said parameter p2, p6, corresponding to a function F(p3) of said parameter p3, and p7, corresponding to a function of two or more of said parameters p1, p2, p3.

* * * * *

UNITED STATES PATENT AND TRADEMARK OFFICE
CERTIFICATE OF CORRECTION

| | | |
|---|---|---|
| PATENT NO. | : 7,935,072 B2 | Page 1 of 1 |
| APPLICATION NO. | : 12/124516 | |
| DATED | : May 3, 2011 | |
| INVENTOR(S) | : Claudio Tonelli | |

It is certified that error appears in the above-identified patent and that said Letters Patent is hereby corrected as shown below:

In claim 1, col. 8, line 28, "and capable of" should read --programmed to--.

Signed and Sealed this
Twenty-first Day of June, 2011

David J. Kappos
*Director of the United States Patent and Trademark Office*